United States Patent
Hjertman et al.

[11] Patent Number: 5,873,856
[45] Date of Patent: Feb. 23, 1999

[54] LIMITED DEPTH PENETRATION NEEDLE HOUSING

[75] Inventors: Birger Hjertman, Vällingby; Rudolf Cseke, Sollentuna; Bohdan Pavlu, Nacka, all of Sweden; Guido Hertig, Fraubrunnen, Switzerland

[73] Assignee: Pharmacia AB, Stockholm, Sweden

[21] Appl. No.: 667,146

[22] Filed: Jun. 20, 1996

[30] Foreign Application Priority Data

Jun. 22, 1995 [SE] Sweden .................................. 9502285

[51] Int. Cl.⁶ ..................................... A61M 5/00
[52] U.S. Cl. ........................ 604/117; 604/192; 604/198
[58] Field of Search .................... 604/117, 198, 604/171, 192, 197

[56] References Cited

U.S. PATENT DOCUMENTS

| | | | |
|---|---|---|---|
| 3,890,971 | 6/1975 | Leeson et al. | 604/198 X |
| 4,235,234 | 11/1980 | Whitney et al. | 604/117 |
| 4,655,751 | 4/1987 | Harbaugh | 604/198 |
| 4,693,708 | 9/1987 | Wanderer et al. | 604/198 |
| 4,840,185 | 6/1989 | Hernandez | 604/198 X |
| 4,894,055 | 1/1990 | Sudnak | 604/198 |
| 4,900,311 | 2/1990 | Stern et al. | 604/198 |
| 4,908,023 | 3/1990 | Yuen | 604/198 |
| 4,929,237 | 5/1990 | Medway | 604/198 |
| 5,026,353 | 6/1991 | Bartman | 604/198 X |
| 5,141,496 | 8/1992 | Dalto et al. | 604/117 |
| 5,183,465 | 2/1993 | Xanthakos et al. | 604/117 X |
| 5,241,969 | 9/1993 | Carson et al. | 604/117 X |
| 5,250,026 | 10/1993 | Ehrlich et al. | 604/117 X |
| 5,364,362 | 11/1994 | Schulz | 604/198 X |
| 5,417,662 | 5/1995 | Hjertman . | |

FOREIGN PATENT DOCUMENTS

| | | |
|---|---|---|
| 95/01804 | 1/1995 | WIPO . |
| 9502285-1 | 6/1995 | WIPO . |
| 95/26750 | 10/1995 | WIPO . |

Primary Examiner—Danton D. DeMille
Attorney, Agent, or Firm—Gilberto M. Villacorta; Pepper Hamilton LLP

[57] ABSTRACT

Disclosed are methods and means for facilitating injection which enable a correct penetration depth of the needle. These improvements are obtainable by using a needle covering device comprising an axially displaceable first tubular sleeve (30) arranged around the front part of said injection apparatus which at its foremost part surrounds the needle (11) over its entire length, and while overcoming a spring force, is axially displaceable rearwards to expose a predetermined length of the needle, said device further comprises a stationary outer tubular sleeve (40) releasably attached to the injection apparatus and fitted around the front part of said injection apparatus and an inner adjustable tubular stopping sleeve (20) which is axially displaceable between at least two predetermined positions while performing a sliding, helical motion around said front part of said injection apparatus when setting the distance between the foremost part of said stopping sleeve and a stopping flange (31) arranged on the inside of the axially displaceable first sleeve.

7 Claims, 3 Drawing Sheets ns which must be over-
come by the user when pressing the needle covering device
against the injection site in order to obtain a subcutaneous
penetration of the needle. It is preferable to design the needle

LIMITED DEPTH PENETRATION NEEDLE HOUSING

The present invention is related to facilitating injection, especially subcutaneous injection by providing a means and methods which enable a correct penetration depth of the needle and thereby to achieve a correct therapeutical effect from the injected drug even if the injection site is altered by the patient.

It is highly desirable for a manufacturer and supplier of pharmaceuticals to meet the demands from patients who are confined to a long time regimen of administration by self-injections. Such patents require safe and convenient equipment which to the highest possible extent will liberate them from the burden of repeated drug taking by injections. It must also be considered that many such patients are elderly or of infant age and might have a reduced physical strength and a strong aversion of needles. Many attempts have therefore been made to provide injection devices which hide or cover the needle for the user and only exposes it at the moment of administration. These devices also have also the advantage that they cover the needle from inadvertent contamination before administration and also provide safety from accidental needle sticks from a used needle. Another requirement of self-injections is that they must be repeatable in order to provide the patient with a correct dose of the pharmaceutical. Since the bioabsorption may vary considerably for a given drug depending on the whether it is administered subcutaneously or intramuscularly, it is of high importance to have a fixed penetration depth of the needle for repeated injections. An inaccurate injection depth may even in certain applications lead to varied effect of the drug which for example for a diabetic dependent on insulin might have fatal consequences.

A means which can be used on an injection device for limiting the penetration of the needle which also entirely covers the needle for the user is disclosed in the International patent application PCT/SE92/00596. With this needle cover it is, however, not possible to adjust the penetration depth of the needle, which is a drawback especially when it is desired to inject the drug into the subcutaneous fat layer. A penetration depth adjustment is especially advantageous when injecting drugs subcutaneously, because the subcutaneous fat layer not only varies considerably between individual patients, it also varies between different parts of an individual body, for example between the thigh, the abdominal area, the arms and the legs. For many drugs, especially polypeptides or proteins like insulin, factor VIII and human growth hormone, also the bioabsorption may vary considerably between intramuscular and subcutaneous administration and also many times locally between different subcutaneous injection sites. In addition, many such drugs might demonstrate an improved activity when administered subcutaneously such as the factor VIII-preparations disclosed in the International patent applications WO 95/01804 and PCT/SE95/00348.

It would therefore be a significant improvement in convenience and safety for many patients to obtain an injection device which can give them a higher freedom to select and alter the injection site, while retaining a correct injection depth for each administration so a repeated drug effect is maintained.

It would also be an improvement to be able to benefit from the advantages of subcutaneous administration and be able to freely select subcutaneous injection sites based on individual desire.

An object of the present invention is to provide a device which maintains all the advantages of a needle covering device while also making it possible to readily adjust the needle penetration depth between different pre-set values. This object is attained by the needle covering device as defined herein.

It is also an object of the present invention to provide a method of adjusting the penetration depth of the needle of an injection apparatus.

Another object of the present invention is to provide an improved method of administering a drug by subcutaneous injection so that a correct penetration depth of the injection needle in the subcutaneous fat layer of patient always is obtained.

A further object of the invention is to provide a kit for subcutaneous injection comprising an injection apparatus and a tubular needle covering device attachable thereto, by means of which a correct subcutaneous injection can be obtained irrespective of the injection site.

A preferred embodiment of the present invention is now described in detail with reference to the appended drawings.

Figure 1:
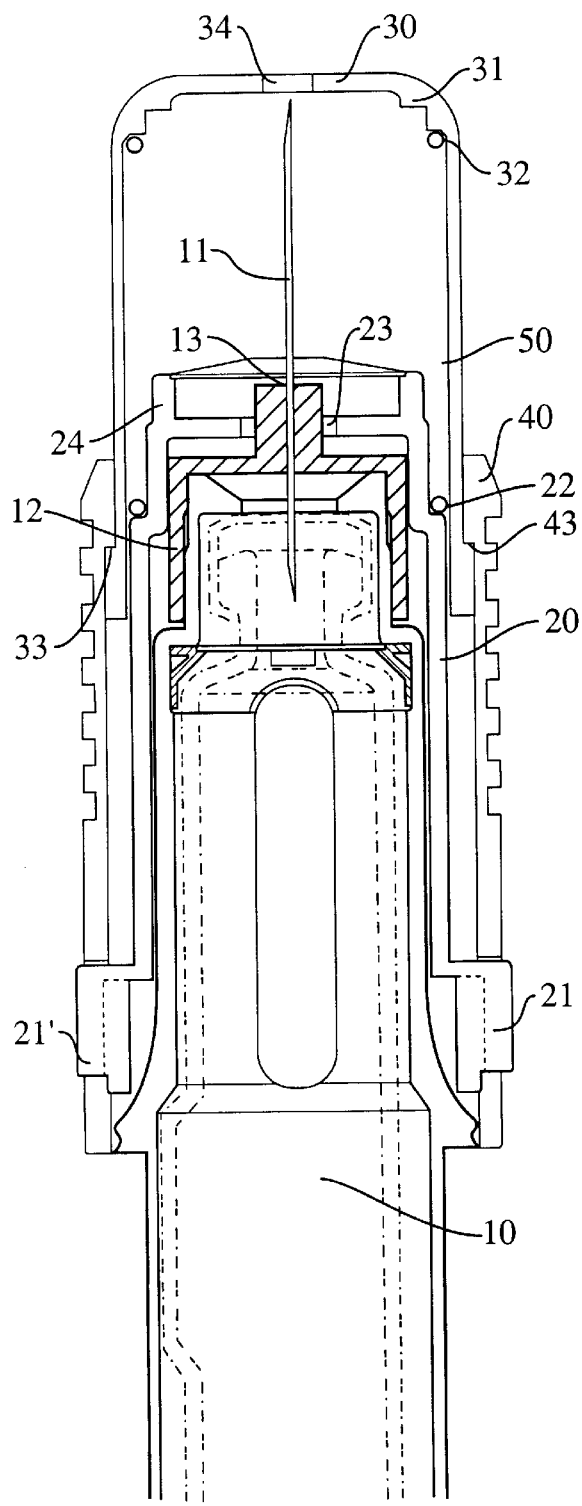
FIG. 1 shows a needle covering device providing a pre-set penetration depth, according to the present invention, before administration.

FIG. 1 shows a front end of an injection apparatus 10 having a needle 11 attached to its foremost end with a needle attachment device of a conventional design, providing that the needle is in liquid communication with the subcutaneously injectible drug. The injection apparatus may be a conventional single dose syringe or an injection pen containing multiple doses connected to a dosing device. The injection apparatus as such is not a part of the present invention and a wide variety of such devices are understood to be possible to use with the present invention if they are provided with suitable attachment means to an adjustable needle covering apparatus according to the invention. In the arrangement of FIG. 1, the injection apparatus is attached to an outer stationary tubular sleeve with a releasable attachment device (not shown) which preferably is snap-lock device of a conventional type. Other types of attachment devices are well-known to the skilled person and will not be discussed in further detail. The outer tubular sleeve 40 is connected to a first axially displaceable sleeve 30 which in FIG. 1 is in its foremost position with a flange 33, resting on a shoulder part 43 of stationary sleeve 40. In this position, the first tubular sleeve 30 covers the needle entirely. Furthermore, the needle covering device comprises an inner adjustable stopping sleeve 20 having a slotted front part through which the needle and its attachment device extends, said front part also is provided with protruding stopping means 24 which co-operates with stopping flange 31 on the inside of sleeve 30 whereby limiting the penetration depth of needle during injection. Between a flange part 32 inside the axially displaceable sleeve 30 and a shoulder part 22 of the stopping sleeve 20 a helical spring device 50 is extended which surrounds the front part of the injection apparatus. The spring device has a spring force which must be overcome by the user when pressing the needle covering device against the injection site in order to obtain a subcutaneous penetration of the needle. It is preferable to design the needle covering device so a major part of the helical spring device (50) is in a position rear of the point (13) where the needle protrudes from the attachment device (12) at the moment of injection. Such a design causes a major part of the needle to be used for the injection and a more comfortable administration for the patient is achieved. At the rear end of the stopping device, diametrically opposite protrusions 21, 21' extend through correspondent slits in the outer stationary sleeve. These features will be explained in more detail below.

Figure 2:
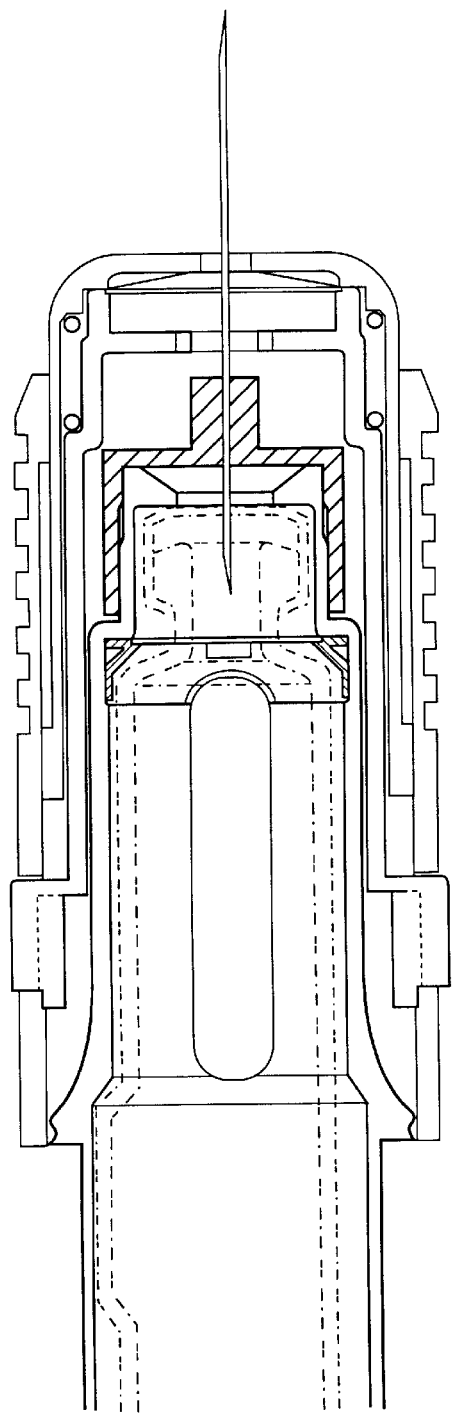
FIG. 2 shows the device according to FIG. 1 during the administration with a first shorter penetration depth of the needle.

To administer a dose from the injection apparatus the needle covering device is pressed gently against the injection site and then by overcoming the spring force of the spring device 50, the stopping device 24 will meet the stopping flange 31, while the needle is forced out through the aperture 34 of the sleeve 30 for a predetermined distance identical to the set distance between said device 24 and flange 31 in resting position, see FIG. 2. After actuating the injection apparatus in a conventional manner to expel and administer a given drug quantity, the spring force can return the needle cover device to the position shown in FIG. 1.

Figure 3:
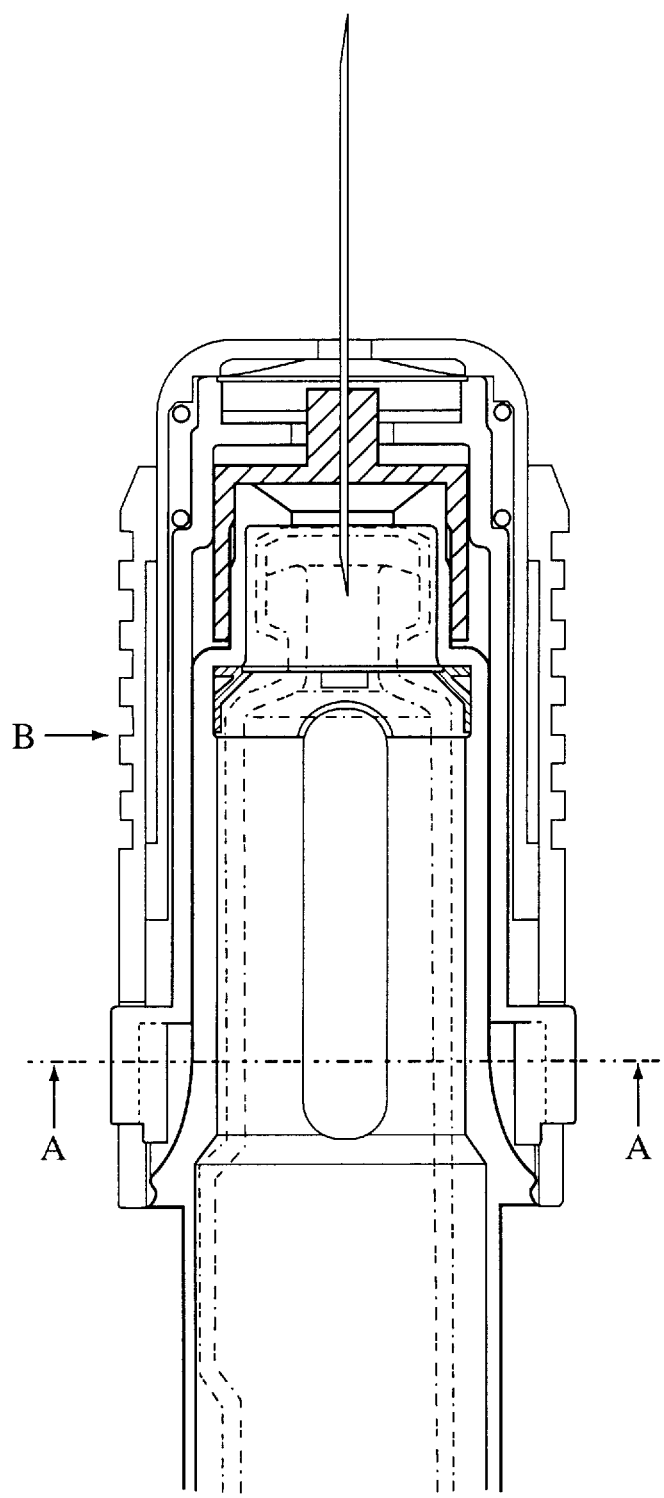
FIG. 3 shows the device according to FIG. 1 with a second longer penetration depth of the needle.
Figure 4:
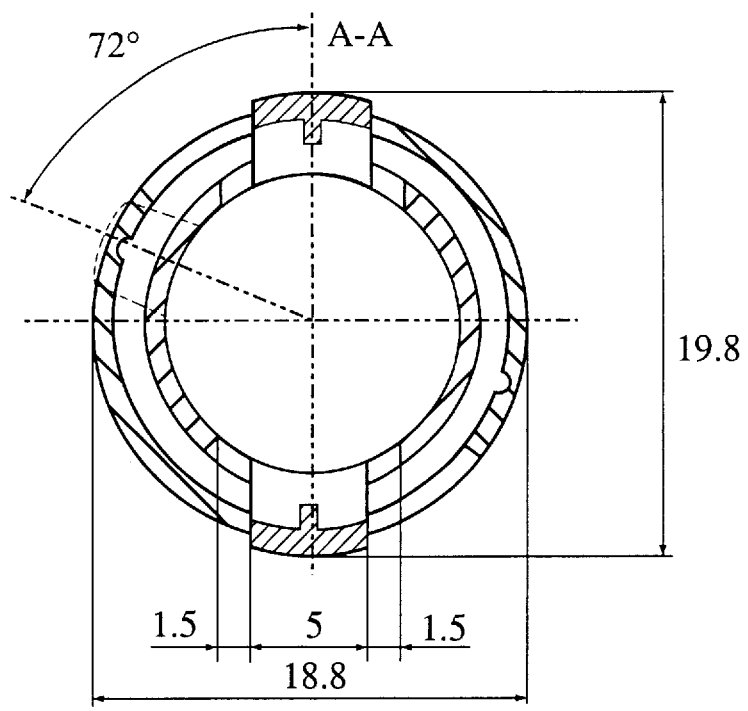
FIG. 4 shows a cross-section of the device according to FIG. 3 in the direction A—A.
Figure 5:
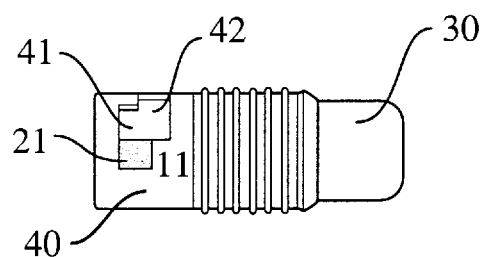
FIG. 5 shows a side view of a needle covering device according to the present invention in a natural size.

A new penetration depth can be set by axially displacing the stopping sleeve 40 between its predetermined positions while it performs a sliding helical motion around the front part of the injection apparatus so a new distance between the foremost part of the stopping sleeve and the stopping flange 31 arranged on the inside of the axially displaceable first sleeve 30, is achieved. The foremost part of the stopping sleeve is preferably an annular stopping flange 24 which hits the preferably annular stopping flange 31 in the stopping position. As best seen in FIG. 5, the setting of a new penetration depth is performed by moving diametrically opposite protrusions 21, 21' of the stopping sleeve simultaneously in the slits 41, 42 and the diametrically opposite slits 41',42', not shown in FIG. 5, of the outer stationary sleeve 40, wherein said protrusions are slidingly fitted, see also FIG. 4 which is a cross-sectional view through the slits. When selecting the longer penetration depth of the needle, as demonstrated in FIG. 3, the protrusions 21, 21' are slidingly moved from the slits 42, 42' to the slits 41, 41' while the stopping sleeve performs helical motion around the injection apparatus. It is to be understood that more slits than demonstrated in FIG. 5 can be used, in order to obtain more than two predetermined penetration depths of the needle. The arrangement with diametrically opposite slits and protrusions shall be regarded as a preferred embodiment of the present invention. The form and number of protrusion and slits may be varied within the scope of the invention to obtain the desired penetration depths that will fit a certain therapeutical application.

Also there are other ways of axially displacing a stopping sleeve between predetermined positions to fix the axial distance between its foremost part and an axially displaceable spring loaded needle covering first sleeve to obtain corresponding pre-set penetration depths into the subcutaneous fat layer. The injection needle of an injection apparatus can be connected to said sleeves by means other than said protrusions and slits and these are also part of the present invention.

In many applications it is advantageous to provide the injection apparatus to the user without the needle attached thereto in the form of a ready-to-use kit together with the needle cover device. The patient can readily attach the needle cover device to the injection apparatus after removing a temporary needle protecting device and can adjust the needle cover to a certain desired injection depth that corresponds to a subcutaneous injection site. It is preferred that the patient selects suitable penetration depths corresponding to selected subcutaneous injection sites after discussion with a physician, since the depth of the subcutaneous fat layer varies between different individuals.

The adjustable needle cover device of the present invention shall not be regarded as limited for subcutaneous administration, since it can be made equally useful for other forms of administration by injection.

We claim:

1. A needle device for adjusting a penetration depth of a needle connected to an injection apparatus, comprising:

an injection apparatus comprising a needle axially protruding from a front part thereof;

an axially displaceable first tubular sleeve arranged around a front part of said injection apparatus, wherein said sleeve comprises a foremost part that surrounds the needle over its entire length;

a compression spring disposed within said foremost part of said first tubular sleeve adapted to be in compressive relationship with said front part of said injection device;

wherein said injection apparatus and said tubular sleeve are axially displaceable with respect to each other and are adapted, by said axial displacement, to expose a predetermined length of needle through said foremost part of said first tubular sleeve;

an outer tubular sleeve releasably attached to, and stationary with respect to, the injection apparatus disposed around at least a portion of the front part of said injection apparatus; and an adjustable inner tubular stopping sleeve axially displaceable between at least two predetermined positions with respect to said front part of said injection apparatus; and a stopping surface arranged on the inside of the axially displaceable first sleeve and adapted to engage with said inner adjustable tubular stopping sleeve;

whereby said axial displacement sets different distances between the foremost part of said stopping sleeve and said stopping surface, and thereby sets different needle length protrusions from the front of said first tubular sleeve.

2. A device according to claim 1, wherein said spring is a helical spring.

3. A device according to claim 2, wherein said helical spring extends between a shoulder part of the stopping sleeve and an inwardly directed flange of first sleeve.

4. A device according to claim 2 wherein when said inner tubular stopping sleeve engages with said stopping surface, a major part of the helical spring is disposed rearwardly of the point where the needle protrudes.

5. A device according to claim 1 wherein the stationary outer sleeve has at least two radially extended slits, wherein said stopping sleeve has at least one protrusion that is adapted to engage with said slits, and wherein said slits are disposed in an axially spaced relationship whereby engagement of said protrusion with each of said slits permits said needle to protrude a different distance.

6. A method of adjusting a penetration depth of a needle of an injection apparatus, which apparatus comprises:

an axially moveable injection apparatus, comprising an axially disposed needle, surrounded by a first tubular sleeve;

an inner stopping sleeve, comprising a foremost part, connected to said first tubular sleeve;

an outer stationary sleeve connected to said first tubular sleeve; and a stopping surface disposed inside the first tubular sleeve and adapted to engage said foremost part of said stopping sleeve;

wherein said method comprises:

helically moving said stopping sleeve between at least two predetermined positions around a front part of said injection apparatus; and thereby setting a distance between the foremost part of said stopping sleeve and said stopping surface which distance corresponds to a selected needle penetration depth.

7. A method according to claim 6, further comprising:

engaging said stopping sleeve with the stationary sleeve by fitting at least one protrusion on said stopping sleeve with radially arranged axially spaced slits on said first tubular sleeve; and slidingly moving said sleeves relative to each other.

* * * * *